United States Patent [19]

Mormann et al.

[11] Patent Number: 4,745,212

[45] Date of Patent: May 17, 1988

[54] PROCESS FOR THE PRODUCTION OF ISOCYANATES

[75] Inventors: Werner Mormann, Kreuztal; Edith Hissmann, Holte-Stukenbrock, both of Fed. Rep. of Germany

[73] Assignee: Bayer Aktiengesellschaft, Leverkusen, Fed. Rep. of Germany

[21] Appl. No.: 105,833

[22] Filed: Oct. 8, 1987

[30] Foreign Application Priority Data

Oct. 8, 1986 [DE] Fed. Rep. of Germany ....... 3634248

[51] Int. Cl.$^4$ ...................... C07C 69/00; C07C 71/00
[52] U.S. Cl. .................................... 560/130; 560/129; 560/138; 560/139; 560/141; 560/142; 560/144; 560/145; 560/336
[58] Field of Search ............... 560/130, 336, 129, 138, 560/139, 141, 142, 144, 145

[56]  References Cited

PUBLICATIONS

Yoshio Iwakura, et al, Journal of Organic Chemistry, vol. 31, 1966, pp. 142–146.
M. Lalonde, T. H. Chan, Use of Organosilicon Reagents as Protected Groups in Organic Synthesis, CA 104:168509, pp. 817–845.

*Primary Examiner*—Alan Siegel
*Attorney, Agent, or Firm*—Gene Harsh; Joseph.C. Gil; Lyndanne M. Whalen

[57]  ABSTRACT

Isocyanates containing ester and/or amide groups are produced by reacting (a) an isocyanatocarboxylic acid chloride with (b) an organic compound containing a silylated alcoholic group and/or silylated phenolic hydroxyl group and/or silylated amino group which compound contains no other group which is reactive with isocyanate and chlorocarbonyl groups under the reaction conditions. The reaction of (a) with (b) is carried out at a temperature of from −20° to 150° C. This process makes it possible to produce the desired isocyanates with a high degree of selectivity.

8 Claims, No Drawings

PROCESS FOR THE PRODUCTION OF ISOCYANATES

BACKGROUND OF THE INVENTION

This invention relates to a new process for the production of isocyanates containing ester and/or amide groups in which (a) isocyanatocarboxylic acid chlorides and (b) organic hydroxy and/or amino compounds in silylated form are used as the starting materials.

The reaction of isocyanatocarboxylic acid chlorides with alcohols or amines is known (Iwakura et al., J. Org. Chem. 31 (1966), 142). However, the selectivity of the reaction is poor. For example, the reaction of an isocyantocarboxylic acid chloride with ethanol in a molar ratio of 1:1 gives isocyanatocarboxylic acid esters in admixture with the corresponding urethane and unchanged isocyanatocarboxylic acid chloride:

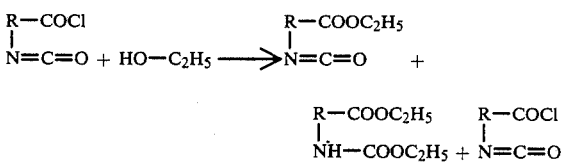

This lack of selectivity has until now been an obstacle to the use of the reaction on an industrial scale.

SUMMARY OF THE INVENTION

It has now been found that isocyanatocarboxylic acid chlorides may be selectively converted into the corresponding isocyanatocarboxylic acid esters or amides if the reactants used are not the compounds containing free hydroxyl groups or amino groups but silylated derivatives thereof.

DETAILED DESCRIPTION OF THE INVENTION

The present invention relates to a process for the production of isocyanates containing ester and/or amide groups in which a) an isocyanatocarboxylic acid chloride is reacted with b) an organic compound which contains at least one silylated alcoholic and/or phenolic hydroxyl group and/or at least one silylated amino group and which is otherwise inert to isocyanate and chlorocarbonyl groups under the reaction conditions at a temperature of from $-20°$ C. to $+150°$ C.

Any organic compound which contains at least one isocyanate group and at least one chlorocarbonyl group and which, apart from the chlorocarbonyl group, is inert to silylated hydroxyl groups or amino groups may be used as component a) in the process of the present invention. Suitable compounds of this type include compounds corresponding to the general formula OCN-R-COCl in which
R represents an aliphatic hydrocarbon radical containing from 2 to 5 carbon atoms with at least 2 carbon atoms being arranged between the isocyanate group and the chlorocarbonyl group.

Examples of particularly preferred isocyanatocarboxylic acid chlorides of this type are 3-isocyanatopropionic acid chloride, 4-isocyanatobutyric acid chloride and 6-isocyanatocaproic acid chloride.

In addition to these preferred isocyanatocarboxylic acid chlorides, it is also possible to use compounds corresponding to the above general formula in which R represents an aliphatic hydrocarbon radical containing more than 6 carbon atoms, an aromatic hydrocarbon radical or a cycloaliphatic hydrocarbon radical. Examples of such isocyanatocarboxylic acid chlorides include 12-isocyantododecanoic acid chloride, 4-isocyanatobenzoic acid chloride and 4-isocyantocyclohexane carboxylic acid chloride.

Isocyanatocarboxylic acid chlorides containing more than one isocyanate group and/or more than one carboxylic acid chloride group are also suitable. Isocyanatocarboxylic acid chlorides such as these include 2,4-diisocyanatobenzoic acid chloride, 2,6-diisocyanatocaproic acid chloride and 2-isocyanatoglutaric acid dichloride. However, the use of such compounds containing more than one isocyanate and/or chlorocarbonyl group is less preferred.

Any organic compound which contains at least one alcoholic or phenolic hydroxyl group in silylated form and/or at least one primary or secondary amino group in silylated form and which, apart from these groups, is inert to isocyanate and chlorocarbonyl groups may be used as component b) in the process according to the invention. Particularly suitable compounds of this type include those corresponding to the general formula $[R'_3Si-X]_m R''$ in which
R' represents an aliphatic hydrocarbon radical containing from 1 to 4 carbon atoms, preferably a methyl group,
R'' represents an m-functional aliphatic hydrocarbon radical containing from 1 to 18 (preferably from 1 to 6) carbon atoms, a cycloaliphatic hydrocarbon radical containing from 4 to 15 (preferably from 6 to 13) carbon atoms or an aromatic hydrocarbon radical containing from 6 to 13 carbon atoms,
X represents oxygen or a group corresponding to the formula —NR'''—, in which R''' represents hydrogen or an alkyl radical, particularly a methyl radical and more preferably hydrogen and
m represents an integer of from 1 to 4, more especially of from 2 to 4.

Compounds suitable for use as component b) include primary, secondary and tertiary alcohols such as methanol, ethanol, n-butanol, isobutanol, tert.-butanol, 1,4-dihydroxybutane, 1,6-dihydroxyhexane, neopentyl glycol, trimethylolpropane and pentaerythritol which are trialkylsilyl-substituted at the alcoholic oxygen atoms; phenols such as phenol, cresol, bisphenol-A, 4,4'-dihydroxy-diphenyl, hydroquinone, resorcinol, 4-hydroxybenzoic acid-hydroquinone-monoester, 4,4'-dihydroxy-diphenylsulfone, 1,5-, 2,6-, 2,7-dihydroxynaphthaline, 2,2-bis-(3,5-dichloro-4-hydroxyphenyl)-propane, 1,1-bis(4-hydroxyphenyl)-cyclohexane, 2,2'-dihydroxy-1,1'-dinaphthyl, 1,3,5-trihydroxybenzene or isocyanato-phenols such as 4-hydroxyphenyl isocyanate, which are trialkylsilyl-substituted at the phenolic hydroxy groups; primary or secondary amines such as n-butylamine, aniline, 1,2-diaminoethane, 1,4-diaminobutane, 1,6-diaminohexane, 4,4'-diaminodiphenylmethane, 2,4-diaminotoluene, 2,6-diaminotoluene, 1,4-diaminobenzene, 1,4-diaminocyclohexane, bis-(aminomethyl)-hexahydro-4,7-methanoindane, 4,4'-diaminodiphenylethane, 4,4'-diamino-diphenylsulfone, 1,4-,1,5-, 2,6-, 2,7-, diaminonaphthalene, 2,2′,5,5′-tetrachlorobenzidine, 3,3′-dimethyl-benzidine, 2,2-bis-(4-aminophenyl)-propane, 1,1-bis-(4-aminophenyl)-cyclohexane and N-methylaniline which are trialkylsilyl-substituted at the amino groups. Other compounds suitable for use as component b) include aminoalcohols such as aminoethanol and 2-aminobutanol which are silylated at the nitrogen and oxygen atoms, heterocyclic compounds containing secondary amino groups in silylated form such as silylated piperazine and substituted alcohols or amines containing silylated hydroxyl or amino groups, such as silylated chloroethanol and silylated aminocarboxylic acids.

The starting materials to be used in silylated form as component b) may be silylated in known manner by reaction of the corresponding compounds containing hydroxyl and/or amino groups with chlorosilanes or disilazanes corresponding to one of the following formulae $$R'_3SiCl$$

or $$R'_3Si-NH-SiR'_3.$$

In these two general formulae, R′ is as defined above. However, the nature of the substituent R′ has no real bearing on the workability of the process according to the invention, because the corresponding triarylsilyl derivatives for example could also be used as component b). Such derivatives are however less preferred.

The starting materials containing hydroxyl and/or amino groups are silylated by methods known to those skilled in the art and described, for example by M. Lalonde and C. H. Chan in *Synthesis* (1985), pages 817–845.

The reaction taking place in the process of the present invention may be represented by the following equation:

$$m \; OCN-R-COCl + [R'_3Si-X]_{\overline{m}}R'' \rightarrow [OCN-R-CO-X]_{\overline{m}}R'' + m \; R'_3SiCl$$

In the practical application of the process of the present invention, the quantity in which reactants a) and b) are used is generally selected so that, for every mole of chlorocarbonyl groups in component a), there is at least 0.8 mole of silylated hydroxyl and/or amino groups present. The quantities in which the reactants are used are preferably selected so that, for every mole of chlorocarbonyl groups in component a), there are from 0.8 to 1.2 moles silylated amino and/or hydroxyl groups. The reaction is most preferably carried out using equimolar quantities (molar ratio of the reactive groups=1:1). Although it would be possible to use one of the two components in an excess beyond the range of 0.8 to 1.2 moles, this would merely result in losses of yield. It is only in the special case where a selective reaction may be required, for example of aminoalcohols with silylated amino and hydroxyl groups to produce isocyanatocarboxylic acid amides containing silylated hydroxyl groups, that the silylated hydroxyl groups are not taken into account in the calculation of the quantitative ratios of the reactants in accordance with the foregoing observations.

The corresponding chlorosilane is formed as a secondary product in the reaction according to the invention. It may readily be separated off by distillation and used for another silylation.

In the case of the silylated alcohols and phenols, the reaction which takes place during the process of the present invention generally occurs at a temperature in the range of from 50° to 150° C. The end of the reaction is readily discernible from the disappearance of the acid chloride carbonyl band at 1800 cm$^{-1}$ in the infra-red spectrum. The corresponding reaction of the silylated amines generally takes place at a temperature in the range of from −20° C. to +50° C. and preferably at a temperature of from −10° C. to +20° C.

The reaction may be carried out in the absence or presence of a suitable solvent. Suitable solvents include diethyl ether, toluene, xylene, trichloroethylene, ethyl acetate, butyl acetate and mixtures of these solvents.

The monoisocyanates (m=1) containing ester or amide groups obtainable by the process of the present invention are interesting intermediate products for organic syntheses, particularly syntheses of pest control agents. The polyisocyanates (m=2–4) obtainable by the process of the present invention are valuable starting materials for the production of polyurethane plastics. The products containing aliphatically or cycloaliphatically bound isocyanate groups obtained by the process of the present invention are particularly suitable for the production of one- or two-component polyurethane lacquers. The functionality of these polyisocyanates may be adapted to the particular application envisaged not only by appropriate choice of the starting materials a) and b), but also by using mixtures of different starting materials a) and/or b). Some of the diisocyanates based on phenols or bisphenols exhibit LC-properties.

The invention is further illustrated but is not intended to be limited by the following examples in which all parts and percentages are by weight unless otherwise specified.

EXAMPLES

EXAMPLE 1 (3-isocyanatopropionic acid phenyl ester)

In a 100 ml three-necked flask equipped with an internal thermometer, a magnetic stirring rod, a dropping funnel and a reflux condenser, 0.1 mole phenoxytrimethyl silane was added dropwise to 0.1 mole isocyanatopropionic acid chloride and stirred for one hour at 140° C. The trimethyl chlorosilane formed was then removed and the crude product purified by distillation.

Yield of 3-isocyanatopropionic acid phenyl ester: 87%.

Bp.: 100° C. at 0.04 mbar.

IR spectrum: V(NCO)=2280 cm$^{-1}$, V(C=0)=1750 cm$^{-1}$

EXAMPLE 2 (12-isocyanatododecanoic acid methyl ester)

0.1 mole 12-isocyanatododecanoic acid chloride was reacted as in Example 1 with 0.11 mole methoxytrimethyl silane at 75° C. until the acid chloride band at 1800 cm$^{-1}$ had disappeared. The desired product was obtained after distillation.

Yield of 12-isocyanatododecanoic acid methyl ester: 67%.

Bp.: 100° C. at 1.3×10$^{-6}$ mbar (flash distillation).

IR spectrum: V(NCO)=2270 cm$^{-1}$, V(C=0)=1740 cm$^{-1}$

EXAMPLES 3 to 5

Reaction with silylated diols

In a 100 ml nitrogen flask, isocyanatocarboxylic acid chloride was added to 0.05 mole silylated alcohol in a quantity of 0.06 mole per functional group of the alcohol, followed by heating for about 30 hours at 80° to 100° C. until the acid chloride band had virtually disappeared. The product was then purified by short-path distillation in a high vacuum.

EXAMPLE 3

1,4-bis-3-isocyanatopropionic acid tetramethylene ester was made by reacting 3-isocyanatopropionic acid chloride and o,o'-bis-trimethylsilyl tetramethylenediol.
Yield: 92%
Bp.: 165° C. at $9.3 \times 10^{-6}$ mbar
IR spectrum: $V(NCO)=2280$ cm$^{-1}$, $V(C=O)=1730$ cm$^{-1}$

EXAMPLE 5

1,4-bis-6-isocyanatocaproic acid tetramethylene ester was made by reacting 6-isocyanatocaproic acid chloride and the silylated diol of Example 3.
Yield: 87%
Bp.: 190° C. at $9.3 \times 10^{-6}$ mbar
IR spectrum: $V(NCO)=2280$ cm$^{-1}$, $V(C=O)=1730$ cm$^{-1}$

EXAMPLES 6 to 8

The procedure was as described for Examples 3-5.

EXAMPLE 6

Trimethylolpropane-tris-(3-isocyanatopropionic acid ester) was made by reacting 3-isocyanatopropionic acid chloride and o,o',O''-tris-trimethylsilyl trimethylolpropane.
Yield: 90%
IR spectrum: $V(NCO)=2280$ cm$^{-1}$, $V(C=O)=1735$ cm$^{-1}$

EXAMPLE 7

Trimethylolpropane-tris-(4-isocyanatobutyric acid ester) was made by reacting 4-isocyanatobutyric acid chloride and the silylated triol of Example 6.
Yield: 95%
IR spectrum: $V(NCO)=2280$ cm$^{-1}$, $V(C=O)=1735$ cm$^{-1}$

EXAMPLE 8

Trimethylolpropane-tris-(6-isocyanatocaproic acid ester) was made by reacting 6-isocyanatocaproic acid chloride and the silylated triol of Example 6.
Yield: 90%
IR spectrum: $V(NCO)=2280$ cm$^{-1}$, $V(C=O)=1735$ cm$^{-1}$

EXAMPLES 9 to 11 (Reaction with silylated tetrahydric alcohols)

The procedure used in each of these examples was the same as that described for Examples 3-5.

EXAMPLE 9

Pentaerythritol tetrakis(3-isocyanatopropionic acid ester) was made by reacting 3-isocyanatopropionic acid chloride and o,o',o'',o'''-tetrakis-trimethylsilyl pentaerythritol.
Yield: 90%
IR spectrum: $V(NCO)=2270$ cm$^{-1}$, $V(C=O)=1739$ cm$^{-1}$

EXAMPLE 10

Pentaerythritol tetrakis-(4-isocyantobutyric acid ester) was made by reacting 4-isocyanatobutyric acid chloride and the silylated tetrol of Example 9.
Yield: 85%
IR spectrum: $V(NCO)=2280$ cm$^{-1}$, $V(C=O)=1740$ cm$^{-1}$

EXAMPLE 11

Pentaerythritol tetrakis-(6-isocyanatocaproic acid ester) was made by reacting 6-isocyanatocaproic acid chloride and the silylated tetrol of Example 9.
Yield: 80%
IR spectrum: $V(NCO)=2280$ cm$^{-1}$, $V(C=O)=1740$ cm$^{-1}$

EXAMPLES 12 to 14 (Reaction with silylated amines and aminoalcohols)

EXAMPLE 12 (6-isocyanatocaproic acid-N-butyl amide)

0.1 mole isocyanatocaproic acid chloride in 150 ml anyhydrous toluene was introduced into a 250 ml reaction flask equipped with an internal thermometer, magnetic stirring rod and dropping funnel. The mixture was cooled to $-5°$ C., followed by the dropwise addition of 0.1 mole n-butyl aminotrimethyl silane, the temperature being kept below 5° C. On completion of the reaction, the mixture was stirred for 30 minutes at room temperature. Toluene was removed by distillation and the product was subsequently purified in a high vacuum in a bulb tube distillation apparatus.
Yield of 6-isocyanatocaproic acid-N-butyl amide: 78%
IR spectrum: $V(NCO)=2280$ cm$^{-1}$, $V(NH)=3300$ cm$^{-1}$ and 1650 cm$^{-1}$

EXAMPLE 13

6-isocyanatocaproic acid-N-(2-trimethylsiloxyethyl)-amide was made from O,N-bis-trimethylsilyl-2-aminoethanol and 6-isocyanatocaproic acid chloride by the procedure described in Example 12.
Yield: 76%
Bp.: 155° C. at $5.3 \times 10^{-6}$ mbar,
IR spectrum: $V(NCO)=2280$ cm$^{-1}$, $V(NH)=3300$ cm$^{-1}$ and 1650 cm$^{-1}$

EXAMPLE 14

6-isocyanatocaproic acid-N-(4-trimethylsiloxybutyl)-amide was made from O,N-bis-trimethylsilyl-4-aminobutanol and 6-isocyanatocaproic acid chloride by the procedure described in Example 12.
Yield: 81%
Bp.: 165° C. at $5.3 \times 10^{-6}$ mbar
IR spectrum: $V(NCO)=2280$ cm$^{-1}$, $V(NH)=3300$ cm$^{-1}$ and 1650 cm$^{-1}$

EXAMPLES 15 to 17 (Preparation of linear polyurethanes by reaction of diester diisocyanates with 1,4-butanediol)

0.02 mole 1,4-butanediol, 15 ml anhydrous chlorobenzene and 0.02 mole of a diester diisocyanate were combined in a 50 ml spherical flask equipped with a magnetic stirring rod and a reflux condenser. The cloudy liquid mixture became clear on heating to 95° C. The clear mixture was then refluxed for another hour at 140°

C., after which the polyurethane was precipitated hot in methanol, filtered under suction and dried at 60° C. in an oil pump vacuum.

EXAMPLE 15

The 1,4-bis-3-isocyanatopropionic acid tetraethylene methylene ester obtained in Example 3 was reacted with 1,4-butanediol in accordance with the procedure described above. Staudinger index (=intrinsic viscosity or limiting viscosity number (LVN) determined in acetone at 25°): $[\eta]=55{,}0\,(ml/g)$ IR spectrum: V(NCO)=no band,
V(C=O)=1730 cm$^{-1}$, V(NH)=3340 cm$^{-1}$ and 1540 cm$^{-1}$ DSC measurement: (DSC=differential scanning calorimetry): endothermic peak at 93°C.

EXAMPLE 16

The 1,4-bis-4-isocyanatobutyric acid tetramethylene ester obtained in Example 4 was reacted with 1,4-butanediol in accordance with the procedure described above. Staudinger index (as determined in acetone at 25° C.): $[\eta]=59.7\ (ml/g)$ IR spectrum: V(NCO)=no band,
V(C=O)=1725 cm$^{-1}$, V(NH)=3320 cm$^{-1}$ and 1540 cm$^{-1}$ DSC measurement: endothermic peak at 93° C.

EXAMPLE 17

The 1,4-bis-6-isocyanatocaproic acid tetraethylene ester obtained in Example 5 was reacted with 1,4-butanediol in accordance with the procedure described above. Staudinger index (as determined in acetone at 25° C.): $[\eta]=106.6\ (ml/g)$ IR spectrum: V(NCO)=no band,
V(C=O)=1730 cm$^{-1}$, V(NH)=3320 cm$^{-1}$ and 1540 cm$^{-1}$ DSC measurement: endothermic peak at 103° C.

EXAMPLE 18

4-(isocyanatophenylcarboxy)-phenyl isocyanate
Starting materials: 4-isocyanato-benzoylchloride and p-(trimethylsilyloxy)-phenyl isocyanat.
Method: in analogy to example 1
Yield: 70%
LC-properties: within the temperature range of from 119° to 154° C.

EXAMPLE 19

4,4'-bis-(isocyanatoethylcarboxy)-biphenyl
Starting materials: 4,4'-bis-(trimethylsilyloxy)-biphenyl and 3-isocyanatopropionic acid chloride
Method: in analogy to example 1.
Yield: 65%
LC-properties: within the temperature range of from 135° to 160° C.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an isocyanate containing ester and/or amide groups in which
   (a) an isocyanatocarboxylic acid chloride is reacted with
   (b) an organic compound containing at least one silylated alcoholic group, silylated phenolic hydroxyl group and/or silylated amino group which compound contains no other group which is reactive with isocyanate and chlorocarbonyl groups under the reaction conditions at a temperature of from −20° to 150° C.

2. The process of claim 1 in which (a) is represented by the formula

OCN-R-COCl in which
R represents an aliphatic hydrocarbon radical containing from 2 to 5 carbon atoms, provided that at least two carbon atoms are present between the isocyanate group and the acid chloride group.

3. The process of claim 2 in which (b) is represented by the formula $[R'_3Si-X]_m R''$ in which
R' represents a C$_1$–C$_4$ alkyl radical,
R'' represents an m-functional aliphatic hydrocarbon radical containing 1–18 carbon atoms, a cycloaliphatic hydrocarbon radical containing 4–15 carbon atoms or an aromatic hydrocarbon radical containing 6–13 carbon atoms,
X represents oxygen or a group corresponding to the formula

-NR'''- in which
R''' represents hydrogen or an alkyl radical
and m represents an integer of from 1 to 4.

4. The process of claim 3 in which R''' represents hydrogen.

5. The process of claim 1 in which (b) is represented by the formula $[R'_3Si-X]_m R''$ in which
R' represents a C$_1$–C$_4$ alkyl radical,
R'' represents an m-functional aliphatic hydrocarbon radical containing 1–18 carbon atoms, a cycloaliphatic hydrocarbon radical containing 4–15 carbon atoms or an aromatic hydrocarbon radical containing 6–13 carbon atoms,
X represents oxygen or a group corresponding to the formula

-NR'''- which
R''' represents hydrogen or an alkyl radical
and m represents an integer of from 1 to 4.

6. The process of claim 5 in which R''' represents hydrogen.

7. The process of claim 1 in which (b) is a compound containing a silylated alcoholic or silylated phenolic group and the reaction is carried out at a temperature of from 50° to 150° C.

8. The process of claim 1 in which (b) is a compound containing a silylated amine group and the reaction is carried out at a temperature of from −20° to 50° C.

* * * * *